US005555039A

United States Patent [19]

Iki et al.

[11] Patent Number: 5,555,039
[45] Date of Patent: Sep. 10, 1996

[54] EYE MEASURING APPARATUS HAVING AN AUTOMATIC FOGGING PRODUCING MECHANISM AND METHOD THEREOF

[75] Inventors: Yoichi Iki, Kawasaki; Nobuyki Miyake, Yokohama; Yasunori Ueno, Kawasaki, all of Japan

[73] Assignee: Nikon Corporation, Tokyo, Japan

[21] Appl. No.: 518,021

[22] Filed: Aug. 22, 1995

Related U.S. Application Data

[63] Continuation of Ser. No. 192,693, Feb. 7, 1994, abandoned.

[30] Foreign Application Priority Data

Feb. 10, 1993 [JP] Japan .................................... 5-021573
Feb. 10, 1993 [JP] Japan .................................... 5-021574

[51] Int. Cl.⁶ .................................. A61B 3/10; A61B 3/00
[52] U.S. Cl. ........................... 351/205; 351/211; 351/212; 351/247
[58] Field of Search ............................... 851/247, 205, 851/210, 211, 212, 214, 221, 206; 354/62

[56] References Cited

U.S. PATENT DOCUMENTS

| | | | |
|---|---|---|---|
| 4,146,311 | 3/1979 | Murr | 351/24 |
| 4,190,332 | 2/1980 | Body et al. | 351/13 |
| 4,353,625 | 10/1982 | Nohda et al. | 351/13 |
| 4,390,255 | 5/1983 | Nohda et al. | 351/212 |
| 4,431,278 | 2/1984 | Nohda | 351/211 |
| 4,572,628 | 2/1986 | Nohda | 351/212 |
| 4,929,076 | 5/1990 | Masuda et al. | 351/212 |

FOREIGN PATENT DOCUMENTS

| | | |
|---|---|---|
| 62-44489 | 9/1987 | Japan . |
| 4-31690 | 5/1992 | Japan . |

*Primary Examiner*—William L. Sikes
*Assistant Examiner*—Huy Mai

[57] ABSTRACT

An eye measuring apparatus includes a refracting power detector for measuring the refracting power of an eye to be examined, a fogging producer for moving the position of a target image in the direction of the optical axis of the eye to be examined, and a feedback controller for receiving an output from the refracting power detector, and moving the position of the target image in a direction, in which accommodation of the eye to be examined is relaxed, in accordance with refracting power information measured in a predetermined meridian direction of the eye to be examined and astigmatic information of the eye to be examined obtained from refracting power values measured in a plurality of meridian directions of the eye to be examined.

33 Claims, 7 Drawing Sheets

EYE MEASURING APPARATUS HAVING AN AUTOMATIC FOGGING PRODUCING MECHANISM AND METHOD THEREOF

This application is a continuation of application Ser. No. 08/192,693, filed Feb. 7, 1994, now abandoned.

BACKGROUND OF THE INVENTION

1. Field of the Invention

The present invention relates to an eye measuring apparatus and method and, more particularly, to an eye measuring apparatus and method having an automatic fogging producer for effectively relaxing accommodation of visual acuity.

In an optometric apparatus for automatically measuring the refracting power of an eye to be examined, i.e., in a so-called objective eye refracting power measuring apparatus, it is necessary to perform a measurement of the refracting power while the eye to be examined is fixed and relaxed. For this purpose, there has been provided an eye refracting power measuring apparatus having an automatic fogging producer which realizes a state in which an eye to be examined is reliably relaxed (e.g., Japanese Patent Publication No. 62-44489 or 63-6012 (U.S. Pat. No. 4,431,278)).

In this eye refracting power measuring apparatus having the conventional automatic fogging producer of the above sort, a feedback system is constituted by the fogging producer for moving the position of the image of a target with a predetermined shape along the direction of optical axis of an eye to be examined, and a refracting power detector for measuring the refracting power of the eye to be examined. This apparatus further includes a position detector for outputting an alignment signal when the apparatus main body is in a position at which the refracting power of the eye to be examined is measurable, and a devices for activating the feedback system in accordance with this alignment signal. The automatic fogging producer whose feedback system is constituted by the refracting power detector and the fogging producer is arranged such that the fogged state of the target is changed in correspondence with the output from the refracting power detector. That is, since it is possible to detect the refractive state of an eye to be examined and reflect the detection result on the position of the target, the image of the target can be moved in a direction in which the eye to be examined is relaxed.

In this conventional apparatus with the above arrangement, if alignment between an eye to be examined and the apparatus main body is performed even momentarily, the refractive state of the eye in one meridian direction inherent in the apparatus is measured automatically (to be referred to as a preliminary measurement hereinafter). In accordance with the refractive state thus preliminarily measured, the image of the target is initially positioned slightly before the retina of the eye to be examined, i.e., in a direction in which the eye attempts to focus on a far point. Subsequently, when an alignment signal is detected, the fogging producer automatically operates such that the eye to be examined attempts to focus on the far point at any instant. After this automatic fogging operation is repeatedly executed, it is confirmed that the alignment is stably performed and the preliminarily measured refractive state is stabilized, and the refracting power of the eye is normally measured for all meridians.

To accurately measure the refracting power while the eye to be examined is in a relaxed state, the above operation is simply repeated for several cycles, thereby performing the normal measurement for the refracting power in all meridian directions of the eye a plurality of times.

As described above, in the eye refracting power measuring apparatus having the conventional automatic fogging producer, the normal measurement for the refracting power of an eye to be examined is merely repeated independently a plurality of times. Therefore, the preceding normal measurement value is not at all reflected on the subsequent automatic fogging operation. In other words, the automatic fogging operation depends on only the preliminary measurement value of refracting power measured in a predetermined meridian direction inherent in the apparatus. For this reason, in a common eye refracting power measuring apparatus in which the astigmatic information of an eye to be examined cannot be obtained unless the eye refracting power is normally measured in all meridian directions, it is impossible to perform an automatic fogging operation which takes account of the astigmatic information of an eye to be examined.

For example, the focal range of an eye to be examined having a spherical power (spherical degree) S and a cylindrical power (astigmatic degree) C is present between a position corresponding to the spherical power S and a position corresponding to the sum total S+C of the spherical power and the cylindrical power. If, therefore, the cylindrical power C is large and a predetermined meridian direction of a preliminary measurement is close to a meridian direction corresponding to the maximum refracting power of an eye to be examined, a target which is supposed to be moved farther than the far point of the eye finally exists within the focal range of the eye in some cases. This may prolong the fogging operation time, and there is also a possibility that the automatic fogging operation is finished before the eye to be examined relaxes sufficiently.

In addition, when the facts that different patients have different angles of astigmatism axes and the measurement meridian direction for the preliminary measurement is inherent in an apparatus are taken into consideration, the same automatic fogging operation may be performed for patients having largely different cylindrical powers rather than patients having the same cylindrical power.

As described above, in the eye refracting power measuring apparatus having the conventional automatic fogging producer, the degree of astigmatism of an eye to be examined is not taken into account at all in the automatic fogging operation. Therefore, for an eye to be examined with a large cylindrical power, the fogging operation becomes time-consuming, and relaxation of the eye is also insufficient.

Recently, an eye measuring apparatus has been developed which can continuously measure the refracting power and the corneal shape of an eye to be examined. In such an eye measuring apparatus, so-called an autorefkeratometer which is a combination of an eye refracting power measuring apparatus (refractometer) and a corneal shape measuring apparatus (keratometer), it is necessary to perform a refracting power measurement while an eye to be examined is fixed and relaxed. For this purpose, as disclosed in Japanese Patent Publication No. 4-31690, there has been provided an eye measuring apparatus having an automatic fogging producer which realizes a state in which an eye to be examined is stably relaxed.

When a measurement of the eye refracting power is to be performed by the above eye measuring apparatus having the conventional automatic fogging producer, a target is set in a fogged state, and the refracting power is measured while an eye to be examined is fixed and relaxed. Subsequently, in a measurement of the corneal shape, the target is positioned by referring to the measured eye refracting power such that the target is clearly seen by the eye to be examined, and the corneal shape is measured while the eye is forced to gaze steadily at the center of the target.

In an eye measuring apparatus having an automatic fogging producer, measurements of the refracting power and the corneal shape of an eye to be examined are generally performed a plurality of times in order to avoid an erroneous measurement in a condition in which fixation and relaxation of the eye are unsatisfactory, and to improve the accuracy of measurement values. In the above conventional eye measuring apparatus, however, in a measurement of the corneal shape, the target is so positioned as to be clearly seen by an eye to be examined, and the eye is forced to gaze steadily at the center of the target. Therefore, the eye to be examined readily falls into a visual acuity accommodation state. Consequently, the influence of the accommodation of visual acuity remains in a measurement of the eye refracting power performed next to make the fogging operation time-consuming, and this makes it difficult to reliably measure an eye refracting power with a high accuracy.

SUMMARY OF THE INVENTION

It is an object of the present invention to provide an eye measuring apparatus and an eye measuring method which can shorten a fogging time by reflecting the astigmatic information of an eye to be examined obtained from a normal measurement value on an automatic fogging operation, and also can reliably measure the eye refracting power of an eye to be examined with a high accuracy by sufficiently relaxing the eye.

It is another object of the present invention to provide an eye measuring apparatus and an eye measuring method which can maintain the relaxed state of an eye to be examined and reduce a fogging time for a measurement of the eye refracting power by performing a measurement of the corneal shape without causing the eye to perform accommodation of visual acuity, thereby reliably measuring both the eye refracting power and the corneal shape with a high accuracy.

In order to achieve the above objects, an eye measuring apparatus of the present invention comprises a refracting power detecting unit for measuring the refracting power of an eye to be examined, a fogging unit for moving the position of a target image in the direction of an optical axis of the eye to be examined, and a feedback control unit for receiving an output from the refracting power detecting means, and moving the position of the target image in a direction, in which accommodation of the eye to be examined is relaxed, in accordance with refracting power information measured in a predetermined meridian direction of the eye to be examined and astigmatic information (more specifically, a spherical power and an a cylindrical power) of the eye to be examined obtained from refracting power values measured in a plurality of meridian directions, and preferably all meridian directions of the eye to be examined.

An eye measuring method according to the present invention comprises the steps of performing a first preliminary measurement of a refracting power in a predetermined meridian direction of an eye to be examined, performing a first fogging operation for sequentially moving a target image in a direction, in which accommodation of the eye to be examined is relaxed, on the basis of the value of the first preliminary measurement, performing a first normal measurement of refracting powers in a plurality of meridian directions of the eye to be examined, performing a second preliminary measurement of a refracting power in a predetermined meridian direction of the eye to be examined, performing a second fogging operation for sequentially moving the target image in a direction, in which accommodation of the eye to be examined is relaxed, on the basis of astigmatic information of the eye to be examined obtained from the values of the normal measurement and a change in the value of the second preliminary measurement with respect to the value of the normal measurement in the predetermined meridian direction, and performing a second normal measurement of refracting powers in a plurality of meridian directions of the eye to be examined.

In the first and second normal measurements, it is desirable to perform the refracting power measurement in all meridian directions.

More preferably, a spherical power (spherical degree) (S) and a cylindrical power (astigmatic degree) (C) of the eye to be examined are obtained from the value of the first normal measurement. Subsequently, as an initial position of the target image, a position which is moved from a position selected between a position corresponding to the spherical power (S) and a position corresponding to the sum total (S+C) of the spherical power and the cylindrical power, by a predetermined distance in a direction, in which accommodation of the eye to be examined is relaxed, is set. Thereafter, the second fogging operation is performed by sequentially moving the initial position in accordance with a change in the value of the second preliminary measurement with respect to the value of the normal measurement in the predetermined meridian direction.

In the present invention as described above, on the basis of the value of the eye refracting power measurement in one predetermined meridian direction of an eye to be examined, i.e., on the basis of the value of the preliminary measurement, the fogging operation is performed while the target is sequentially moved to a position obtained by adding to this preliminary measurement value an appropriate fogging value in a direction toward the far point of the eye to be examined. When the fogging operation is ended, a normal measurement of the eye refracting power is performed in all meridian directions of the eye to be examined.

By calculating the spherical power S and the cylindrical power C from the normal measurement value of the eye refracting power, it is possible to know the position of the farthest point (the position corresponding to S) of the eye to be examined and the focal range (which is between the position corresponding to S and the position corresponding to S+C) of the eye. Therefore, a position obtained by adding a proper fogging value to a position closer to some extent than the farthest point, e.g., a position corresponding to an equivalent spherical value S+C/2 in a direction toward the far point of the eye to be examined is set as an initial value, and the target is moved to this initial position. Thereafter, a change $\Delta DH=DHn-DH0$ of each preliminary measurement value DHn with respect to a normal measurement value DH0 in the predetermined meridian direction (e.g., the horizontal direction) is calculated for each preliminary measurement. The automatic fogging operation is then performed by sequentially moving the target to a position apart from the initial position by a distance corresponding to this change $\Delta DH$.

The state of accommodation of visual acuity of an eye to be examined during the fogging operation, i.e., the tendency of the change in preliminary measurement value during the fogging operation can be considered to be almost equal in all meridian directions regardless of the astigmatic state of the eye. Therefore, although only the eye refracting power measurement value in one predetermined meridian direction inherent in an apparatus, i.e., only the preliminary measurement value is actually used, it is possible in the second and subsequent normal measurements to perform a fogging operation nearly equivalent to a fogging operation based on the preliminary measurement value obtained in a meridian direction corresponding to the equivalent spherical value S+C/2 by reflecting the astigmatic information of the eye to be examined.

In the present invention, the preliminary measurement value is not limited to the refracting power in one meridian direction. That is, an arrangement is also possible in which refracting powers in two orthogonal meridians, e.g., a refracting power in a horizontal direction and a refracting power in a vertical direction, can be obtained as preliminary measurement values. In this case, assuming that components in the horizontal and vertical directions obtained by a normal measurement are DH0 and DV0, respectively, and components in the horizontal and vertical directions obtained by a preliminary measurement are DHn and DVn, respectively, average values DA0 and DAn of the components in the horizontal and vertical directions obtained by the normal and preliminary measurements, respectively, are given by:

$$DA0=(DH0+DV0)/2$$

$$DAn=(DHn+DVn)/2$$

By using the average values DA0 and DAn of the components obtained by the normal and preliminary measurements, a change ΔDA in the average value is given by the following equation:

$$\Delta DA=DAn-DA0.$$

The change ΔDA thus calculated may be used in place of ΔDH mentioned earlier.

As described above, the preliminary measurement of the present invention can be performed not only in one meridian direction but also in a plurality of meridian directions. In either case, the measurement is performed in a predetermined meridian direction inherent in an apparatus.

According to the present invention, therefore, the astigmatic information of an eye to be examined obtained by the normal measurement can be reflected on the fogging operation. In other words, the fogging operation can be performed while the positions corresponding to the refracting powers in the strong (first) and weak (second) principal meridian directions of an eye to be examined are taken into account. This makes it possible to shorten the fogging operation time and avoid an event in which the automatic fogging operation is finished before an eye to be examined is relaxed satisfactorily. Consequently, the eye refracting power can be measured accurately and reliably. In the above, the strong (first) principal meridian means the meridian which has a strongest refracting power, and the weak (second) principal meridian means the meridian which has a weakest refractive power. The direction of the strong (first) principal meridian and the direction of the weak (second) principal meridian are perpendicular to each other.

In addition, to achieve the above object of the present invention, an eye measuring apparatus according to the present invention comprises a refracting power detecting unit for measuring the refracting power of an eye to be examined, a fogging unit for moving the position of a target image in the direction of the optical axis of the eye to be examined, a feedback control unit for moving the position of the target image in a direction, in which accommodation of the eye to be examined is relaxed, in accordance with an output from the refracting power detecting unit, and a corneal shape detecting unit for measuring the corneal shape of the eye to be examined while accommodation of the eye to be examined is relaxed by the fogging operation performed by the fogging producing unit.

An eye measuring method according to the present invention is a method of automatically measuring the refracting power and corneal shape of an eye to be examined and comprises the steps of performing a preliminary measurement of a refracting power in a predetermined direction of the eye to be examined, performing a fogging operation for sequentially moving a target image in a direction, in which accommodation of the eye to be examined is relaxed, on the basis of the value of the preliminary measurement, measuring the corneal shape of the eye to be examined while accommodation of the eye to be examined is relaxed during the fogging operation, and performing a normal measurement of refracting powers in a plurality of meridian directions of the eye to be examined.

In the normal measurement of an eye to be examined, it is preferable that the refracting powers be measured in all meridian directions.

In the present invention as described above, on the basis of the eye refracting power measurement value in a predetermined meridian direction of an eye to be examined, i.e., on the basis of the preliminary measurement value, the preliminary fogging operation is performed while the target is sequentially moved to a position obtained by adding an appropriate fogging value to this preliminary measurement value in a direction toward the far point of the eye to be examined. The corneal shape of the eye is measured at a proper timing in this preliminary fogging operation period, e.g., immediately before the end of the preliminary fogging operation period. Subsequently, when the preliminary fogging operation is finished, i.e., when the preliminary measurement value is stabilized, a normal measurement of the eye refracting power is performed in a plurality of meridian directions, and preferably all meridian directions of the eye to be examined. Such a measurement cycle is repeated a predetermined number of times.

In the present invention as described above, since the corneal shape is measured in the preliminary fogging state, accommodation of an eye to be examined is not caused during the corneal shape measurement, so the eye is kept fixed and nearly relaxed. Therefore, the fogging operation to be performed subsequently to the measurement is not adversely affected, and this makes it possible to shorten the fogging time for the eye refracting power measurement. Consequently, both the eye refracting power and the corneal shape can be accurately and reliably measured.

An eye measuring method according to another aspect of the present invention is a method of measuring the refracting power and corneal shape of an eye to be examined and comprises the steps of performing a first preliminary measurement of a refracting power in a predetermined meridian direction of the eye to be examined, performing a first fogging operation for sequentially moving a target image in a direction, in which accommodation of the eye to be examined is relaxed, on the basis of the value of the first preliminary measurement, measuring the corneal shape of the eye to be examined while accommodation of the eye to be examined is relaxed during the first fogging operation, performing a first normal measurement of refracting powers in a plurality of meridian directions of the eye to be examined, performing a first preliminary measurement of a refracting power in a predetermined meridian direction of the eye to be examined, performing a second fogging operation for sequentially moving the target image in a direction, in which accommodation of the eye to be examined is relaxed, on the basis of astigmatic information of the eye to be examined obtained from the values of the first normal measurement and a change in the value of the second preliminary measurement with respect to the value of the normal measurement in the predetermined meridian direction, measuring the corneal shape of the eye to be examined while accommodation of the eye to be examined is relaxed during the second fogging operation, and performing a second normal measurement of refracting powers in a plurality of meridian directions of the eye to be examined.

As described above, in the eye measuring method according to another aspect of the present invention, the astigmatic information of an eye to be examined obtained by the normal measurement can be reflected on the fogging operation. This makes it possible to shorten the fogging operation time and reliably measure the eye refracting power with a high accuracy while the eye to be examined is relaxed satisfactorily.

Other features and advantages of the present invention will become apparent from the following detailed description of the preferred embodiments.

DESCRIPTION OF THE PREFERRED EMBODIMENT

The embodiments of the present invention will be described in detail below with reference to the accompanying drawings.

Figure 1:
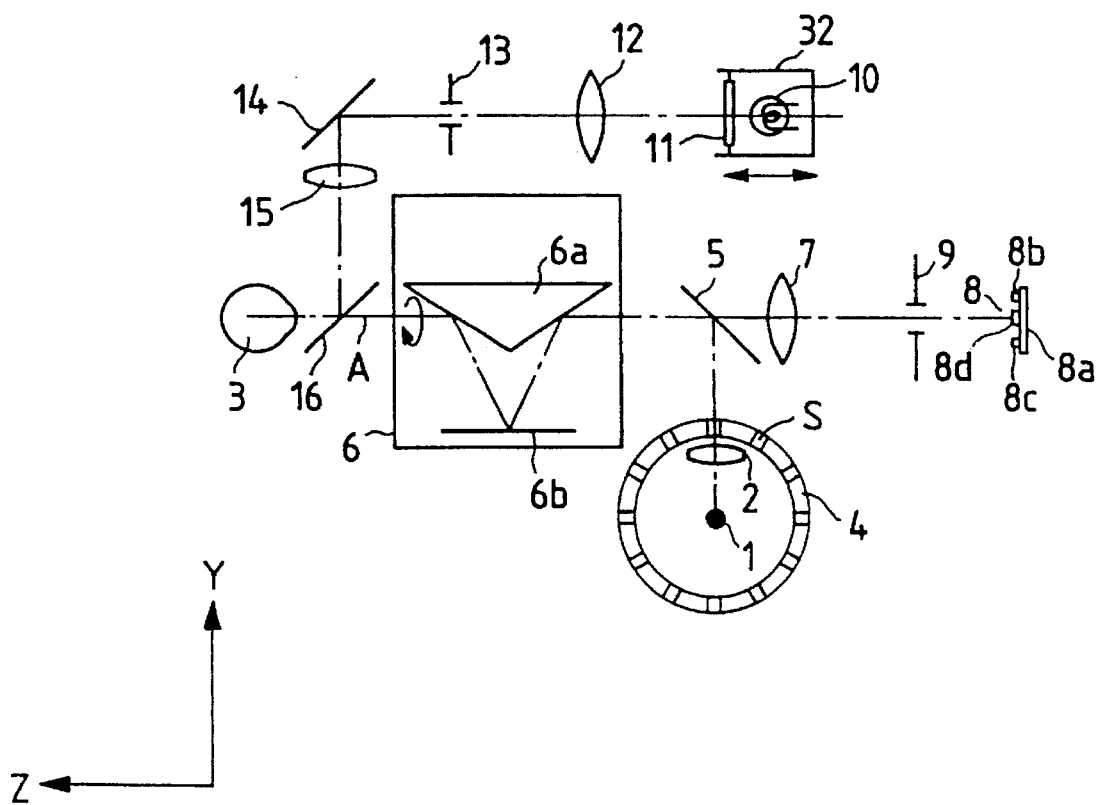
FIG. 1 is a schematic view showing the arrangement of an optical system of an eye refracting power measuring apparatus according to a first embodiment of the present invention.

FIG. 1 is a schematic view showing the arrangement of an optical system of an eye refracting power measuring apparatus according to a first embodiment of the present invention. In the embodiment shown in FIG. 1, the X axis is taken in a direction perpendicular to the plane of the paper, the Y axis is taken in the longitudinal direction of the paper, and the Z axis is taken in the lateral direction of the paper.

The eye refracting power measuring apparatus of this embodiment comprises a refracting power detector and a fogging producer. The measurement principle of this refracting power detector is based on skiascopy; i.e., an eye refracting power is measured by detecting the velocity of the movement of a shadow on a pupil. An objective eye refracting power detector using the skiascopy is disclosed in, e.g., U.S. Pat. No. 4,390,255 (Japanese Laid-Open Patent Application No. 55-86437).

The apparatus shown in FIG. 1 includes a light-emitting diode 1 for emitting infrared light. The image of the infrared light emitted from the light-emitting diode 1 is formed on the pupil of an eye 3 to be examined by the action of a condenser lens 2. The light-emitting diode 1 and the condenser lens 2 are surrounded by a chopper 4 comprising of a hollow cylindrical member. A plurality of slit-like holes S are formed along the circumference of the chopper 4. The longitudinal direction of the holes S is the X-axis direction (perpendicular to the plane of the paper).

The chopper 4 is so designed as to be rotatable about the light-emitting diode 1 by a driving system (not shown). A linear light beam transmitted through the slit-like hole S formed in the chopper 4 is incident on a half mirror 5. The half mirror 5 reflects the infrared light emitted from the light-emitting diode 1 toward the eye 3 to be examined and transmits light reflected by the eye 3 to be examined.

The apparatus shown in FIG. 1 further includes a measurement meridian rotating system 6 comprising of a prism 6a and a mirror 6b. The measurement meridian rotating system 6 is for observing the astigmatic state of the eye 3 to be examined. The meridian direction of the linear light beam to be incident on the eye 3 to be examined is varied by rotating the measurement meridian rotating system 6 about an optical axis A (Z axis).

The light reflected by the eye 3 to be examined passes through the measurement meridian rotating system 6 and the half mirror 5 and enters an objective lens 7. The image of the pupil's plane of the eye 3 to be examined, which is transmitted through the objective lens 7, is formed on a light-receiving unit 8 through a diaphragm 9. The diaphragm 9 has a rectangular hole whose longitudinal direction is the X-axis direction (perpendicular to the plane of the paper). This hole is positioned on nearly the focal point of the objective lens 7.

The light-receiving unit 8 includes a substrate 8a, photoelectric conversion elements 8b and 8c for the refracting power measurement fixed on the substrate 8, and a four-segment photoelectric conversion element 8d for misalignment detection. As is apparent from FIG. 1, the photoelectric conversion elements 8b and 8c are arranged in the scan direction of the linear light beam on the eye 3 to be examined.

Figure 2:
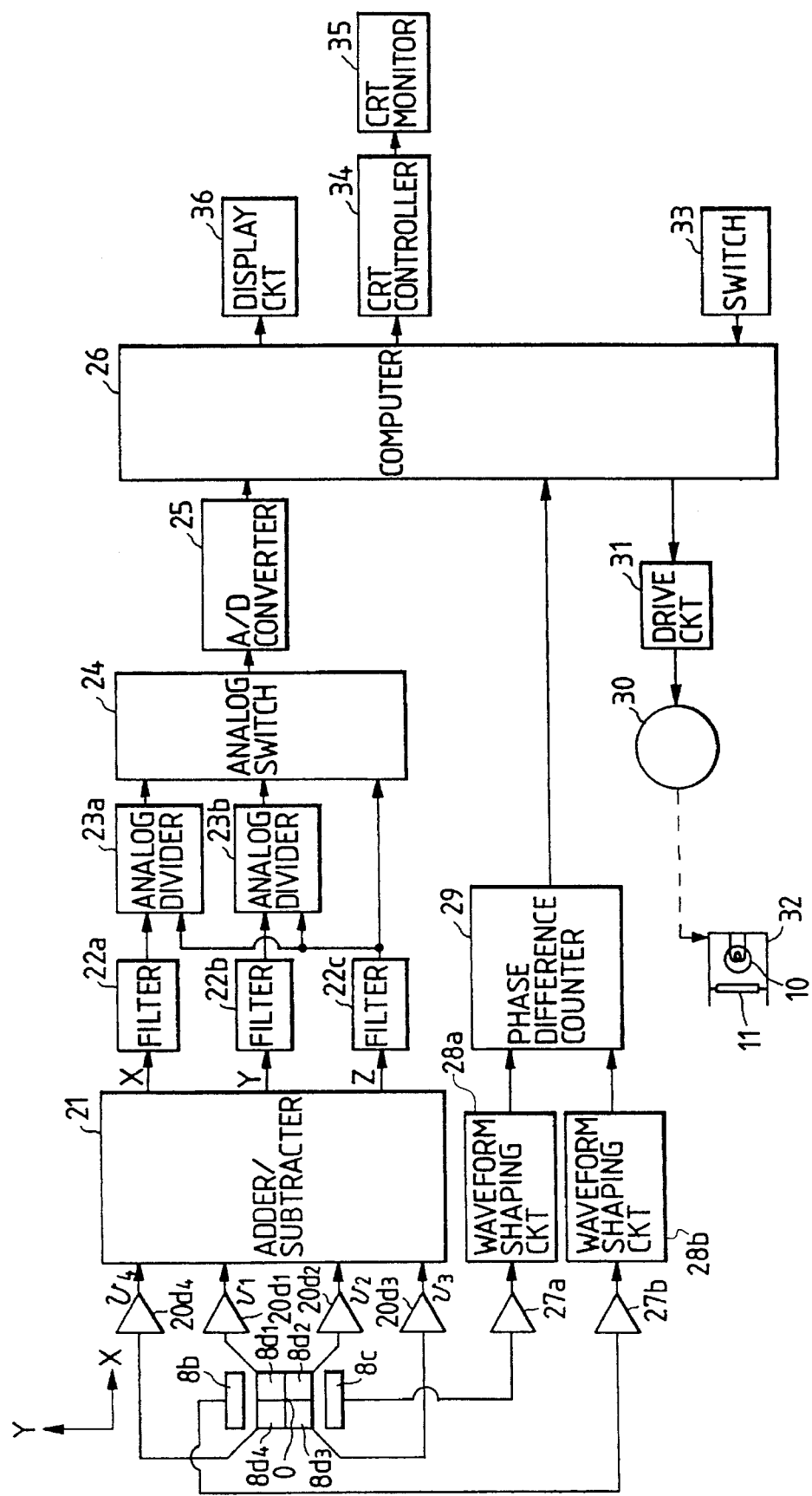
FIG. 2 is a block diagram showing the arrangement of an electrical processing system of the eye refracting power measuring apparatus according to the first embodiment.

As illustrated in FIG. 2 which is a plan view in which the light-receiving unit 8 is viewed in the direction (Z-axis direction) of the objective lens 7, the four-segment photoelectric conversion element 8d arranged between the photoelectric conversion elements 8b and 8c is constituted by four photoelectric conversion elements $8d_1$ to $8d_4$ arranged in the X-Y plane. A center O of the four photoelectric conversion elements $8d_1$ to $8d_4$ is aligned with the optical axis A of the objective lens 7.

As described above, the optical system of the refracting power detector is constituted by the light-emitting diode 1, the condenser lens 2, the chopper 4, the half mirror 5, the measurement meridian rotating system 6, the objective lens 7, the light-receiving unit 8, and the diaphragm 9.

An optical system of the fogging producer, on the other hand, includes a target 11 and a visible light source 10 for emitting visible light rays for illuminating the target 11. The target 11 and the visible light source 11 are integrally held by a holding member 32. This holding member 32 is so arranged as to be movable back and forth in the Z-axis direction (indicated by arrows in FIG. 1) and is driven by a stepping motor 30.

The image of the target 11 illuminated by the visible light source 10 is reflected by a mirror 14 through a projecting lens 12 and a diaphragm 13 and incident on a lens 15. The image of the target 11 passing through the lens 15 is reflected by a half mirror 16 toward the eye 3 to be examined and projected on the retina of the eye 3 to be examined through its lens. The lens 15 sets the diaphragm 13 at a position optically conjugate with respect to the pupil of the eye 3 to be examined. In other words, this action of the lens 15 makes it possible to hold the size of a pupil optically constant regardless of the eye 3 to be examined and consequently keeps the depth of field constant.

If the refractive state of the lens of the eye 3 to be examined is a certain fixed state, the position of the target 11 at which its image is formed on the retina of the eye 3 to be examined is only one particular point on the optical axis. That is, the position of the target 11 on the optical axis, at which the image of the target 11 is formed on the retina, is in a one-to-one correspondence with the refracting power of the lens of the eye 3 to be examined.

As described above, the optical system of the fogging producer is constituted by the visible light source 10, the target 11, the holding member 32, the projecting lens 12, the diaphragm 13, the mirror 14, the lens 15, and the half mirror 16.

FIG. 2 is a block diagram showing the arrangement of an electrical processing system of the eye refracting power measuring apparatus according to this embodiment. A signal processing procedure of the apparatus of this embodiment will be described below with reference to FIG. 2.

Photocurrents produced in the four photoelectric conversion elements $8d_1$ to $8d_4$ upon reception of light are converted into voltage signals with a low impedance by four corresponding amplifiers $20d_1$ to $20d_4$, respectively. The output voltage signals from the amplifiers $20d_1$ to $20d_4$ are applied to an adder/subtracter 21. From the outputs of the four photoelectric conversion elements $8d_1$ to $8d_4$, the adder/subtracter 21 outputs a signal X corresponding to a position difference in the X direction (indicated by an arrow in FIG. 2) of the corneal reflected light, a signal Y corresponding to a positional difference in the Y direction (indicated by an arrow in FIG. 2) of the corneal reflected light, and a sum total signal Z indicating the intensity of the corneal reflected light. Note that the X and Y directions are in a plane perpendicular to the measurement optical axis A.

Assuming that the outputs from the amplifiers $20d_1$ to $20d_4$ are $v_1$ to $v_4$, respectively, the signal X is $(v_1+v_2)-(v_3+v_4)$, and the signal Y is $(v_1+v_4)-(v_2+v_3)$. The chopping frequency components of the three output signals X, Y, and Z from the adder/subtracter 21 are suppressed by low-pass filters 22a, 22b, and 22c, respectively, and these signals are thereby converted into DC voltages. To prevent a coordinate signal from varying in accordance with the difference in corneal reflectance, analog dividers 23a and 23b normalize the signals X and Y, respectively.

The X coordinate signal and the Y coordinate signal thus normalized by the analog dividers 23a and 23b, respectively, and the sum total signal Z are alternately, successively extracted by an analog switch 24. These extracted signals are converted into digital signals by an A/D converter 25 and applied to a computer 26. The computer 26 drives a display circuit 36 to display the X and Y coordinate signals converted into digital signals by the A/D converter 25.

Detection of the refracting power, on the other hand, is performed by measuring the phase difference between output signals from the two photoelectric conversion elements 8b and 8c. That is, since the eye fundus of the eye 3 to be examined is scanned by the linear light beam upon rotation of the chopper 4, the position of each slit 9 exactly corresponds to a neutral point if the eye 3 to be examined is an eye of emmetropia. For this reason, the light beam emitted through the openings of the slits 9 becomes bright or dark uniformly, equalizing the phases of the output signals from the two photoelectric conversion elements 8b and 8c.

If the eye 3 to be examined is not an eye of emmetropia, bright and dark fringes corresponding to the state of the anomaly of refraction of the eye are emitted through the openings of the slits 9. Therefore, the phases of the output signals from the photoelectric conversion elements 8b and 8c differ from each other in accordance with the state of the anomaly of refraction of the eye to be examined. This makes it possible to obtain the refracting power of the eye to be examined from the phase difference between the output signals from the photoelectric conversion elements 8b and 8c.

The outputs from the two photoelectric conversion elements 8b and 8c are applied to buffers 27b and 27a and shaped into square waves by waveform shaping circuits 28b and 28a, respectively. The outputs from the waveform shaping circuits 28b and 28a are converted into a pulse count corresponding to the phase difference by a phase difference counter 29 and applied to the computer 26. The computer 26 alternately receives the signals from the A/D converter 25 and the phase difference counter 29.

When the X and Y signals exhibit nearly zero levels and the sum total signal Z has a predetermined or higher level (this signal serves as an alignment signal), i.e., when alignment between the eye to be examined and the apparatus main body is performed, a predetermined pulse is output as a drive signal to a drive circuit 31 of the stepping motor 30 in accordance with the digital signal output from the phase difference counter 29. In this case, the sum total signal Z is also taken into consideration because the X and Y signals sometimes show nearly zero levels even if the eye to be examined and the apparatus main body are largely misaligned from each other.

The stepping motor 30 drives the member 32 for integrally holding the visible light source 10 and the target 11. As mentioned earlier, the refracting power of the eye 3 to be examined is in a one-to-one correspondence with the position of the target 11 at which its image is formed on the retina of the eye. To relax the eye 3 to be examined, the target image must be formed slightly before the retina so that the eye 3 to be examined attempts to focus on the far point. Taking account of this respect, therefore, the position of the holding member 32, i.e., the position of the target 11 is determined in accordance with a signal (in this embodiment, a signal corresponding to the phase difference between the output signals from the photoelectric conversion elements 8b and 8c) which corresponds to the refracting power of the eye 3 to be examined.

An optometrist confirms that there is no misalignment between the eye 3 to be examined and the apparatus main body and no eyelashes or the like of a patient is present in a measurement optical path. Thereafter, the optometrist turns on a measurement start switch 33 to apply a measurement start signal to the computer 26. Upon receiving the measurement start signal, the computer 26 activates the automatic fogging producer. When a variation in the output from the phase difference counter 29 becomes small to indicate a stabilized state of a feedback system, the computer 26 receives the output signal from the phase difference counter 29, converts the received signal into a diopter, and applies the diopter to a CRT controller 34 of a CRT monitor 35. Consequently, the refracting power (diopter) of the eye to be examined measured while the eye is almost relaxed is displayed on the CRT monitor 35.

Figure 3:
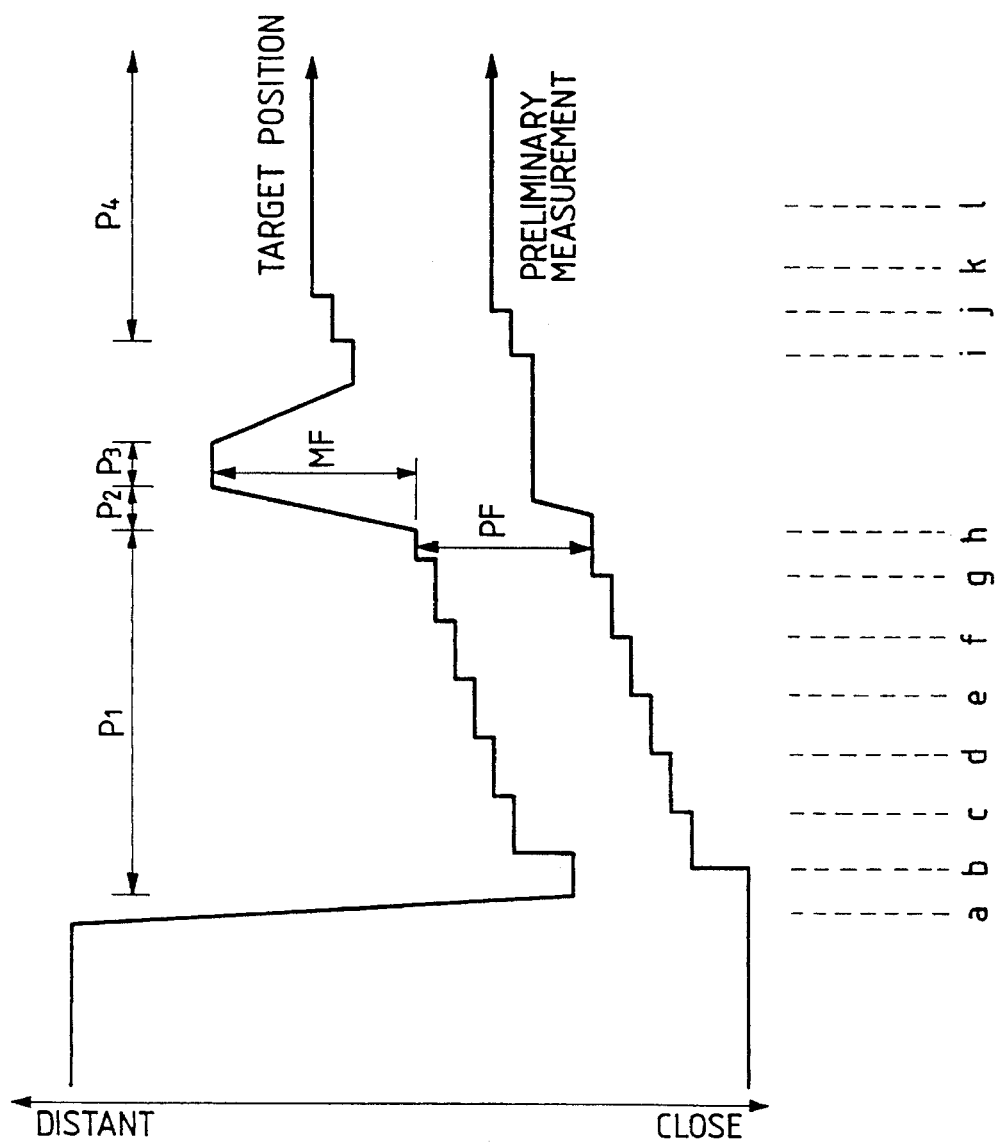
FIG. 3 is a view for explaining the basic operation of the eye refracting power measuring apparatus according to the first embodiment.

FIG. 3 is a view for explaining the operation of the apparatus according to this embodiment.

When a measurement is to be performed for the eye 3 to be examined for the first time, no data concerning the refracting power of the eye 3 to be examined is available. Therefore, the target 11 is initially arranged at a position sufficiently far from most eyes 3 to be examined, e.g., a position of +5 to +6 diopter. In these conditions, the target 11 is seen as a blurred image at a rather distant position for most eyes 3 to be examined. The target 11 is initially arranged at a position which can be sufficiently far from the eye 3 to be examined because the refracting power of an eye readily varies toward a close side, i.e., in the direction of accommodation, and so accommodation of visual acuity occurs if the target is moved from the close side.

Subsequently, the light source for measurement, i.e., the light-emitting diode 1 is made to emit light to check whether the measurement of the eye refracting power is possible. More specifically, it is checked whether alignment between the apparatus main body and the eye 3 to be examined is performed properly based upon the detected X and Y coordinate signals, and it is checked whether the intensity of the reflection signal from the eye 3 to be examined is appropriate based upon the level of the sum total signal Z. If the preliminary measurement is possible, the eye refracting power value (preliminary measurement value) in one meridian direction (e.g., the horizontal direction) of the eye 3 to be examined at this instant (a timing indicated by a in FIG. 3) is measured automatically while the measurement meridian rotating system 6 is fixed at the initial position of that device.

On the basis of the preliminary measurement value thus obtained, the feedback system of the apparatus is operated to move the target 11 in a direction in which the eye 3 to be examined focuses on the far point. That is, in this embodiment, the target 11 is moved to a position (preliminary fogging position) corresponding to a value obtained by adding, e.g., 0.75 diopter as a value (preliminary fogging value) PF to the preliminary measurement value so that the preliminary fogging position becomes far enough.

If the measurement is possible, a preliminary measurement (timings b to g in this embodiment) is subsequently performed automatically, thereby performing the preliminary fogging operation by the above feedback system a plurality of times. As described above, since the target 11 is far from the refractive state of the eye to be examined by the preliminary fogging value PF, the eye 3 to be examined attempts to focus on this target 11. That is, the eye 3 to be examined attempts to relax its accommodation to follow the positional change of the target 11. As a result, the eye to be examined gradually relaxes and eventually, hardly follows the positional change of the target 11. That is, the variation of the preliminary measurement value becomes small and stable (the timing indicated by g in FIG. 3).

An operator depresses a measurement SW at the moment (a timing indicated by h in FIG. 3) he or she confirms that the preliminary measurement value is stable and the alignment is also stable, starting a final fogging operation (main fogging operation) for a normal measurement. The main fogging operation involves moving the target 11 to a position (main fogging position) corresponding to a value obtained by adding, e.g., 1.50 diopter as a value (main fogging value) MF to the value, which is obtained by adding the preliminary fogging value PF to the preliminary measurement value, so that the main fogging position is far enough. If the preliminary fogging operation is repeated for a sufficient time and the degree of astigmatism of the eye 3 to be examined is small, the normal measurement may be performed immediately by omitting the above main fogging operation. If, however, no enough time can be taken for the preliminary fogging operation or the cylindrical power of the eye 3 to be examined is so large that the position of the target is within the focal range of the eye 3 to be examined, accommodation of the eye 3 to be examined is not relaxed satisfactorily. For this reason, it is preferred to perform the main fogging operation for moving the target to a farther position, thereby relaxing the eye to be examined more reliably.

When the above main fogging operation is completed, the measurement meridian rotating system 6 is rotated once to normally measure eye refracting powers in all meridian directions. From the measurement values thus obtained, the computer calculates data concerning the highest refracting power, the lowest refracting power, meridians corresponding to the highest and lowest refracting powers, a spherical power S, a cylindrical power C, and an angle AX of the axis of astigmatism.

A first measurement cycle is thus completed through a preliminary fogging period P1 from the start of the preliminary measurement to the turning on of the measurement SW, a main fogging period P2 for performing the main fogging operation, and a normal measurement period P3. A second measurement cycle is started some time after the first measurement cycle is completed.

At the start point of the second measurement cycle, the data of the astigmatic degree of the eye 3 to be examined which is normally measured in the first measurement cycle is already available. Unlike in the first measurement cycle, therefore, the initial position of the target 11 can be determined by taking into account the astigmatic information of the eye 3 to be examined. The spherical power S and the cylindrical power C are calculated from the preceding normal measurement values, thereby obtaining a position which is closer to some extent from the farthest point of the eye 3 to be examined, e.g., a position which corresponds to an equivalent spherical value S+C/2. A position obtained by adding to this position the preliminary fogging value PF (0.75 diopter in this embodiment) in a direction in which the eye to be examined attempts to focus on the far point is set as an initial position, and the target 11 is moved to this initial position. In this state, a first preliminary measurement is performed automatically at the moment (a timing indicated by i in FIG. 3) the preliminary measurement becomes possible.

Subsequently, a change $\Delta ADH = DH1 - DH0$ of a first preliminary measurement value DH1 with respect to a normal measurement value DH0 in the one meridian direction (e.g., the horizontal direction) is calculated, and the target 11 is moved to a position apart from the initial position by a distance corresponding to this change $\Delta DH$, thereby performing a second preliminary measurement at the next preliminary measurement timing (j in FIG. 3). A change ΔDH=DH2−DH0 of a second preliminary measurement value DH2 is calculated, and the target 11 is moved to a position apart from the initial position by a distance corresponding to this change ΔDH. Thereafter, this process is repeatedly executed to perform the preliminary fogging operation.

In the above-mentioned preliminary fogging operation, the astigmatic information of an eye to be examined obtained in the preceding normal measurement can be reflected on the fogging operation. This makes it possible to extremely shorten a preliminary fogging period P4 and realize the relaxed state of an eye to be examined with a high reliability.

The main fogging operation and the normal measurement operation in the second and subsequent measurement cycles are basically the same as those in the first measurement cycle, and so a detailed description thereof will be omitted. In this manner, the apparatus of the present invention finishes its operation after repeatedly executing the measurement cycle a predetermined number of times.

Figure 4:
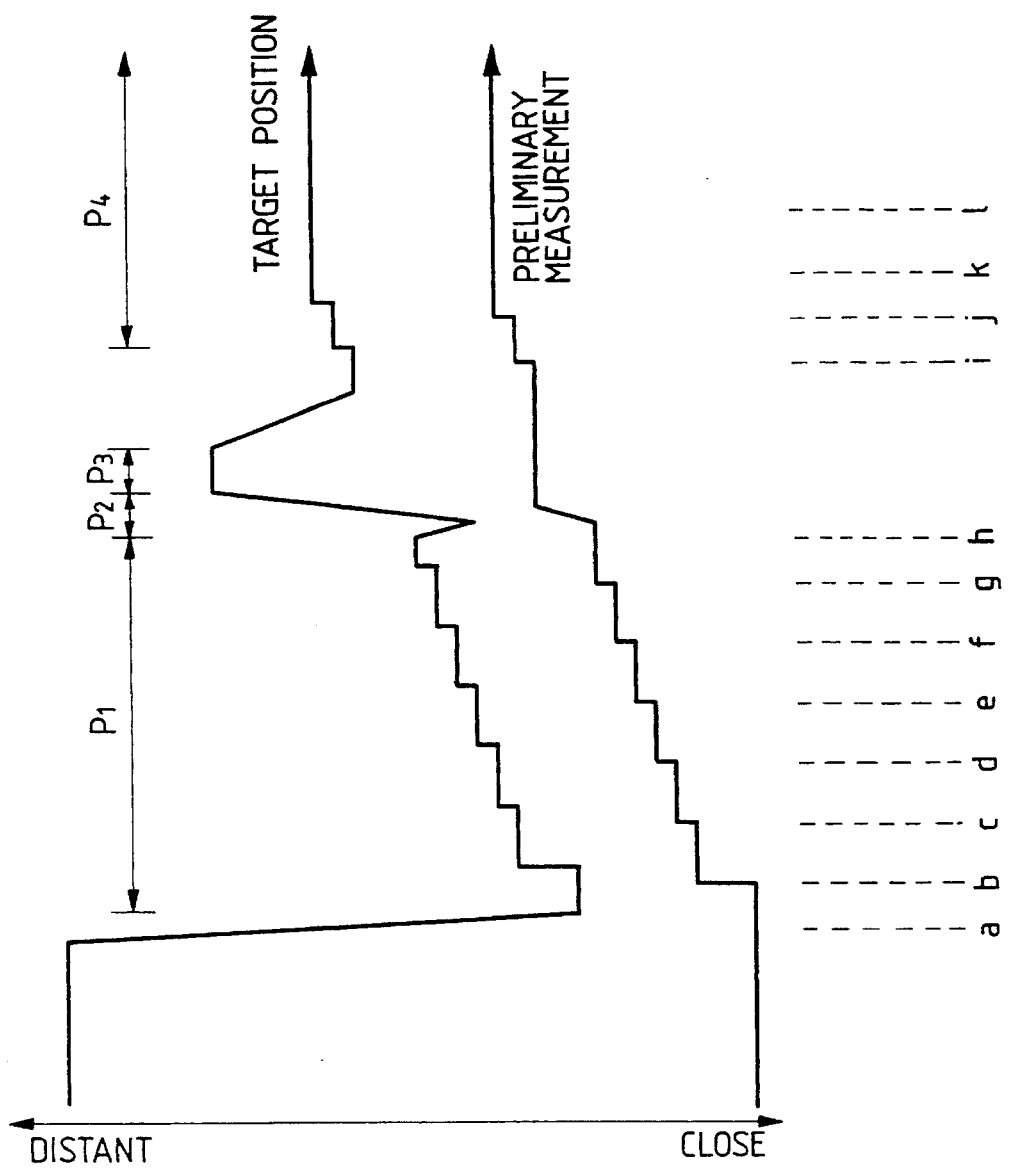
FIG. 4 is a view for explaining a modification of a main fogging operation shown in FIG. 3.

FIG. 4 is a view for explaining a modification of the main fogging operation shown in FIG. 3. In this modification, in the main fogging period P2 after the preliminary fogging period P1, the target is once moved by a predetermined distance in a direction opposite to a direction in which accommodation of an eye to be examined is relaxed, and then moved by a predetermined distance in the direction in which accommodation of the eye to be examined is relaxed. Thereafter, a normal measurement is performed. The interest of the eye to be examined can be attracted on the target by temporarily moving the target closer to the eye to be examined. Therefore, accommodation of the eye to be examined can be relaxed reliably because the eye to be examined attempts to focus on this moving target.

In this embodiment, the main fogging operation is performed by moving the target to the position corresponding to the value obtained by adding the main fogging value MF to the value which is obtained by adding the preliminary fogging value PF to the preliminary measurement value. As described above, however, this main fogging operation is not an essential operation of the present invention. Therefore, if it is difficult for a patient to gaze steadily at the target for an extended period of time since he or she is an infant or has an eye disease, an operator also can perform the normal measurement immediately after the preliminary fogging operation by omitting the main fogging operation, thereby stably measuring the eye refracting power.

Figure 5:
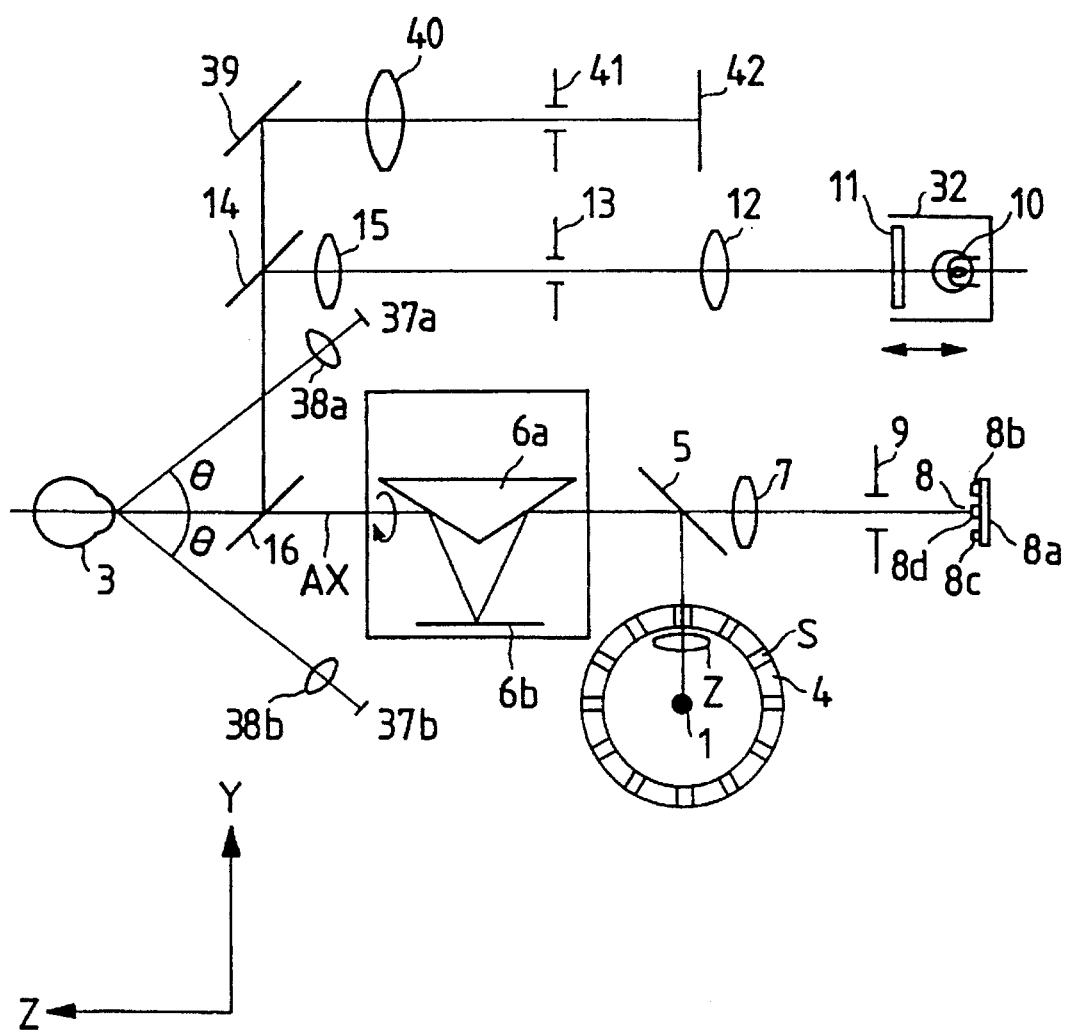
FIG. 5 is a schematic view showing the arrangement of an optical system of an ophthalmological apparatus according to a second embodiment of the present invention.
Figure 6:
FIG. 6 is a plan view showing the eye measuring apparatus according to the second embodiment viewed from an eye to be examined.
Figure 6:
Figure 6:
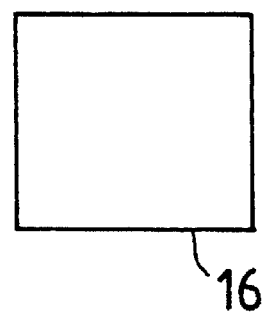
Figure 6:
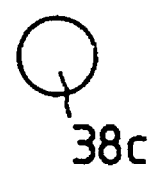
Figure 6:
Figure 6:
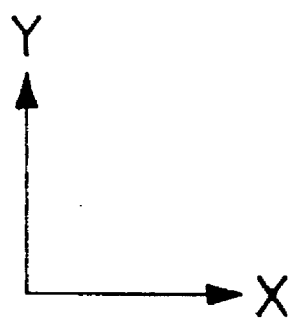

The second embodiment of the present invention will be described below with reference to FIGS. 5 and 6. FIG. 5 is a schematic view showing the arrangement of an optical system of an eye measuring apparatus according to the second embodiment. FIG. 6 is a plan view showing the eye measuring apparatus of FIG. 5 viewed in the Z-axis direction. Note that the same reference numerals as in the first embodiment denote parts having the same functions in this second embodiment. Note also that the same coordinate system as shown in FIG. 1 is used in FIG. 5.

In the second embodiment, the present invention is applied to an eye measuring apparatus for measuring both the refracting power and the corneal shape of an eye to be examined. This apparatus includes a refracting power detector, a fogging producer, and a corneal shape detector. The measurement principle of the refracting power detector is based on skiascopy as in the first embodiment described above.

The eye measuring apparatus according to the second embodiment has the corneal shape detector in addition to the arrangement of the first embodiment. The corneal shape detector of the second embodiment will be described below with reference to FIGS. 5 and 6.

Referring to FIG. 5, an optical system of the corneal shape detector has four projecting optical systems each having an optical axis at an angle 8 with respect to an optical axis AX of an eye 3 to be examined. These projecting optical systems include light sources 37a and 37b and collimator lenses 38a and 38b arranged along the optical axes intersecting the optical axis AX of the eye to be examined at the angle θ in the Y-Z plane. Although only two projecting optical systems are illustrated in FIG. 5, the eye measuring apparatus of this embodiment includes two other projecting optical systems each having an optical axis at the angle θ with respect to the optical axis AX of the eye 3 to be examined in the X-Z plane. As shown in FIG. 6, these projecting optical systems include light sources 37c and 37d and collimator lenses 38c and 38d arranged along optical axes crossing the optical axis AX of the eye to be examined at the angle θ in the X-Z plane.

In other words, as shown in FIG. 6 which is a plan view in which the eye measuring apparatus of this embodiment is viewed from the eye 3 to be examined, the four light sources 37a to 37d and the four corresponding collimator lenses 38a to 38d are positioned about the optical axis AX of the eye 3 to be examined with equal angular spacings between them on the circumference perpendicular to that optical axis.

Light beams emitted from the light sources 37a to 37d are collimated into parallel light beams by the corresponding collimator lenses 38a to 38d and projected onto the cornea of the eye 3 to be examined. That is, the light sources 37a to 37d are positioned at the focal points of the corresponding collimator lenses 38a to 38d.

Referring back to FIG. 5, light reflected by the surface of the cornea of the eye 3 to be examined is reflected by a half mirror 16, transmitted through a half mirror 14, reflected by a mirror 39, and incident on an objective lens 40. A diaphragm 41 is arranged at the rear focal point of the objective lens 40. The image of the reflected light passing through the objective lens 40 is formed on a light-receiving element after passing through the diaphragm 41.

At this point, the light beams emitted from the light sources 37a and 37b through the collimator lenses 38a and 38b, respectively, form two corneal reflected images with a spacing $h_1$ between them on the light-receiving element 42. On the other hand, the light beams emitted from the light sources 37c and 37d through the collimator lenses 38c and 38d, respectively, form two corneal reflected images with a spacing $h_2$ between them on the light-receiving element 42.

The spacings $h_1$ and $h_2$ of these corneal reflected images correspond to the radius of curvature of the cornea in the directions (e.g., the horizontal and vertical directions) of two orthogonal meridians. If the cornea of the eye to be examined is spherical, $h_1=h_2$; if the cornea is toric, $h_1 \neq h_2$. In this arrangement, an element such as a CCD is usable as the light-receiving element 42, and the image spacings $h_1$ and $h_2$ can be obtained from signals corresponding to output coordinates from the element such as a CCD. The radius of curvature of the cornea of the eye 3 to be examined is calculated from the obtained image spacings $h_1$ and $h_2$.

Figure 7:
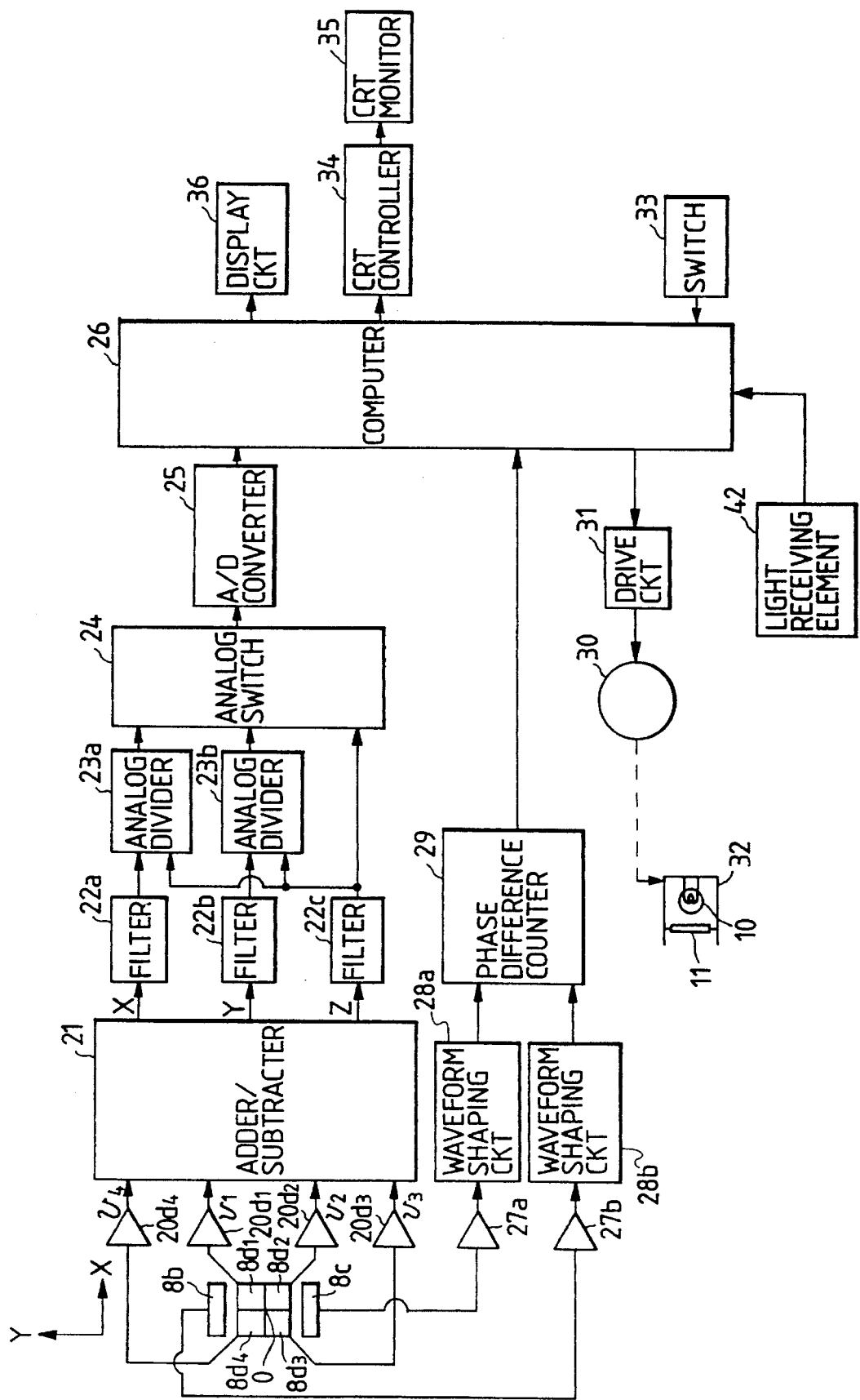
FIG. 7 is a block diagram showing the arrangement of an electrical processing system of the eye measuring apparatus according to the second embodiment.

An electrical processing system of the eye measuring apparatus according to the second embodiment is basically identical with the electrical processing system of the first embodiment illustrated in FIG. 2. Therefore, only the difference from the first embodiment will be described below with reference to FIG. 7 showing the arrangement of the electrical processing system of the second embodiment. Note that the same reference numerals as in the first embodiment shown in FIG. 2 denote parts having the same functions in FIG. 7.

Referring to FIG. 7, in the measurement of a corneal shape, an output signal from the light-receiving element 42 is applied to a computer 26. From this signal, the computer 26 calculates the radius of curvature of a cornea in the directions of two orthogonal meridians of an eye to be examined. Consequently, a CRT monitor 35 outputs the measurement value of the corneal shape of the eye to be examined.

The operation of the eye measuring apparatus according to the second embodiment will be described next. Since, however, the operation of the second embodiment is nearly identical with that of the first embodiment, only a difference in operation will be described with reference to FIG. 3.

In the operation of the eye measuring apparatus of the second embodiment shown in FIG. 3, the measurement of a corneal shape is performed during a preliminary fogging operation (an operation for sequentially moving a target to a position obtained by adding a preliminary fogging value to a preliminary measurement value) indicated by P1. In this case, the corneal shape measurement is desirably performed while alignment between the apparatus main body and the eye 3 to be examined is stable. In this embodiment, therefore, it is preferable that the corneal shape measurement be performed immediately before the end of the preliminary fogging operation P1 (e.g., at a timing indicated by g in FIG. 3), at which timing the eye 3 to be examined is fixed and relaxed.

The corneal shape measurement may also be performed during a preliminary fogging period P4 in a second measurement cycle. In this embodiment, the astigmatic information of the eye 3 to be examined obtained in the preceding normal measurement can be reflected on the fogging operation. This makes it possible to significantly shorten the preliminary fogging period P4 and stably realize the relaxed state of the eye 3 to be examined. In this preliminary fogging period P4, the corneal shape measurement can be performed again while the alignment between the apparatus main body and the eye 3 to be examined is stabilized.

In each of the above embodiments, the preliminary measurement for the eye refracting power is performed in one meridian direction. Instead, it is possible to perform the preliminary measurement of the eye refracting powers in the directions (e.g., the horizontal and vertical directions) of two orthogonal meridians. In this case, assuming that components in the horizontal and vertical directions obtained by a normal measurement are DH0 and DV0, respectively, and components in the horizontal and vertical directions obtained by a preliminary measurement are DHn and DVn, respectively, average values DA0 and DAn of the components in the horizontal and vertical directions obtained by the normal and preliminary measurements, respectively, are given by:

$$DA0 = (DH0 + DV0)/2$$

$$DAn = (DHn + DVn)/2.$$

By using the average values DA0 and DAn of the components obtained by the normal and preliminary measurements, a change ΔDA in the average value is given by the following equation:

$$\Delta DA = DAn - DA0.$$

The change ΔDA thus calculated can be used in place of the change ΔDH of the preliminary measurement value in each embodiment. In this manner, the preliminary measurement in each of the above embodiments can be performed not only in one meridian direction but also in a plurality of meridian directions.

The present invention is not limited to the above embodiments but can take various forms without departing from the spirit and scope of the invention.

What is claimed is:

1. An eye measuring apparatus comprising:

a refracting power detector to measure refracting power values of an eye to be examined in a plurality of meridian directions;

a fogging producing mechanism to move a position of a target image in a direction of an optical axis of the eye to be examined, thereby performing a fogging operation; and a feedback controller to cause said fogging producing mechanism to move the position of said target image in a direction in which accommodation of the eye to be examined is relaxed, in accordance with astigmatic information of the eye to be examined and the refracting power value measured in a predetermined one of the plurality of meridian directions, wherein the astigmatic information is based upon the refracting power values measured in at least two of the plurality of meridian directions and the refracting power value in the predetermined meridian direction takes into account the astigmatic information.

2. An apparatus according to claim 1, wherein said feedback controller performs:

a first preliminary measurement of the refracting power value in the predetermined meridian direction of the eye to be examined, a first fogging operation for sequentially moving said target image in the direction in which accommodation of the eye to be examined is relaxed, based upon the refracting power value of the first preliminary measurement, a first normal measurement of the refracting power values in said at least two meridian directions of the eye to be examined whose accommodation is relaxed by said first fogging operation, a determination of the astigmatic information of the eye to be examined based upon the refracting power values of said first normal measurement, a second preliminary measurement of the refracting power value in the predetermined meridian direction of the eye to be examined, after said target image is moved to a first position based upon the astigmatic information, a second fogging operation for sequentially moving said target image in the direction in which accommodation of the eye to be examined is relaxed, based upon the astigmatic information and the refracting power value measured in said second preliminary measurement, and a second normal measurement of the refracting powers in said at least two meridian directions of the eye to be examined whose accommodation is relaxed by said second fogging operation.

3. An apparatus according to claim 2, wherein said feedback controller:

obtains a spherical power and a cylindrical power of the eye to be examined from the refracting power values of the first normal measurement, sets, as an initial position of said target image, a set position which is moved from a selected position between a second position corresponding to the spherical power and a third position corresponding to a sum total of the spherical power and the cylindrical power, by a predetermined distance in the direction in which accommodation of the eye to be examined is relaxed, and performs the second fogging operation by sequentially moving said target image from the initial position in accordance with a change in the refracting power value of the second preliminary measurement with respect to the refracting power values of the first normal measurement.

4. An apparatus according to claim 3, wherein the selected position corresponds to an equivalent spherical value of the eye to be examined calculated from the refracting power values of the first normal measurement.

5. An apparatus according to claim 2, wherein said feedback controller moves said target image, in said second fogging operation, in the direction in which accommodation of the eye to be examined is relaxed by a predetermined distance from said first position, and then performs said second normal measurement.

6. An apparatus according to claim 2, wherein said feedback controller:

once moves said target image by a first predetermined distance in a direction opposite to the direction in which accommodation of the eye to be examined is relaxed, and then moves said target image by a second predetermined distance in the direction in which accommodation of the eye to be examined is relaxed, to perform a normal measurement.

7. An apparatus according to claim 1, further comprising a corneal shape detector to measure a corneal shape of the eye to be examined while accommodation of the eye to be examined is relaxed by the fogging operation performed by said fogging producing mechanism.

8. An apparatus according to claim 7, wherein said feedback controller performs:

a preliminary measurement of the refracting power value in the predetermined meridian direction of the eye to be examined, a fogging operation for sequentially moving said target image in the direction in which accommodation of the eye to be examined is relaxed, based upon the refracting power value of the preliminary measurement, a measurement of the corneal shape and a normal measurement in said at least two meridian directions of the eye to be examined whose accommodation is relaxed by the fogging operation.

9. An apparatus according to claim 8, wherein said feedback controller performs the measurement of the corneal shape immediately before stopping the fogging operation.

10. An apparatus according to claim 7, wherein said feedback controller performs:

a first preliminary measurement of the refracting power value in the predetermined meridian direction of the eye to be examined, a first fogging operation for sequentially moving said target image in the direction in which accommodation of the eye to be examined is relaxed, based upon the refracting power value of the first preliminary measurement, a measurement of a corneal shape of the eye to be examined whose accommodation is relaxed by the first fogging operation, a first normal measurement of the refracting power values in said at least two meridian directions of the eye to be examined whose accommodation is relaxed by said first fogging operation, a determination of the astigmatic information of the eye to be examined based upon the refracting power values of said first normal measurement, a second preliminary measurement of the refracting power value in the predetermined meridian direction of the eye to be examined, after said target image is moved to a first position based upon the astigmatic information, a second fogging operation for sequentially moving said target image in the direction in which accommodation of the eye to be examined is relaxed, based upon the astigmatic information and the power refracting value measured in said second preliminary measurement, and at least one of a measurement of the corneal shape and a second normal measurement of the refracting powers in said at least two meridian directions of the eye to be examined whose accommodation is relaxed by said second fogging operation.

11. An apparatus according to claim 10, wherein said feedback controller:

obtains a spherical power and a cylindrical power of the eye to be examined from the refracting power values of the first normal measurement, sets, as an initial position of said target image, a set position which is moved from a selected position between a second position corresponding to the spherical power and a third position corresponding to a sum total of the spherical power and the cylindrical power, by a predetermined distance in the direction in which accommodation of the eye to be examined is relaxed, and performs the second fogging operation by sequentially moving said target image from the initial position in accordance with a change in the refracting power value of the second preliminary measurement with respect to the refracting power values of the first normal measurement.

12. An apparatus according to claim 11, wherein the selected position corresponds to an equivalent spherical value of the eye to be examined calculated from the refracting power values of the first normal measurement.

13. An apparatus according to claim 10, wherein said feedback controller moves said target image, in said second fogging operation, in the direction in which accommodation of the eye to be examined is relaxed by a predetermined distance from said first position, and then performs said second normal measurement.

14. An eye measuring apparatus comprising:

a refracting power detector to measure a refracting power value of an eye to be examined;

a fogging producing mechanism to move a position of a target image in a direction of an optical axis of the eye to be examined;

a feedback controller to cause said fogging producing mechanism to move the position of said target image in a direction in which accommodation of the eye to be examined is relaxed, in accordance with the refracting power value from said refracting power detector; and a corneal shape detector to measure a corneal shape of the eye to be examined whose accommodation is relaxed by the fogging operation performed by said fogging producing mechanism.

15. A method of measuring a refracting power and a corneal shape of an eye to be examined, comprising the steps of:

performing a preliminary measurement of a refracting power value in a predetermined meridian direction of the eye to be examined;

performing a fogging operation for sequentially moving a target image in a direction in which accommodation of the eye to be examined is relaxed, based upon the refracting power value of the preliminary measurement; and performing a measurement of a corneal shape and a normal measurement of refracting power values in at least two meridian directions of the eye to be examined whose accommodation is relaxed by said fogging operation.

16. A method according to claim 15, wherein the step of measuring the corneal shape is performed immediately before the fogging operation is stopped.

17. A method of measuring a refracting power and a corneal shape of an eye to be examined, comprising the steps of:

performing a first preliminary measurement of a refracting power value in a predetermined meridian direction of the eye to be examined;

performing a first fogging operation for sequentially moving a target image in a direction in which accommodation of the eye to be examined is relaxed, based upon the refracting power value of the first preliminary measurement;

measuring a corneal shape of the eye to be examined whose accommodation is relaxed by said first fogging operation;

performing a first normal measurement of refracting power values in at least two meridian directions of the eye to be examined whose accommodation is relaxed by said first fogging operation;

determining astigmatic information of the eye to be examined, based upon the refracting power values obtained in said step of performing a first normal measurement;

performing a second preliminary measurement of the refracting power value in the predetermined meridian direction of the eye to be examined after moving said target image to a first position based upon the astigmatic information;

performing a second fogging operation for sequentially moving said target image in a direction in which accommodation of the eye to be examined is relaxed, based upon the astigmatic information and the refracting power value of the second preliminary measurement;

performing at least one of a measurement of the corneal shape and a second normal measurement of the refracting power values in the at least two meridian directions of the eye to be examined whose accommodation is relaxed by said second fogging operation.

18. A method according to claim 17, further comprising the steps of:

obtaining a spherical power and a cylindrical power of the eye to be examined from the refracting power values of the first normal measurement;

setting, as an initial position of said target image, a set position which is moved from a selected position between a second position corresponding to the spherical power and a third position corresponding to a sum total of the spherical power and cylindrical power, by a predetermined distance in the direction in which accommodation of the eye to be examined is relaxed; and performing the second fogging operation by sequentially moving said target from the initial position in accordance with a change in the refracting power value of the second preliminary measurement with respect to the refracting power values of the first normal measurement.

19. A method according to claim 18, wherein the selected position corresponds to an equivalent spherical value of the eye to be examined calculated from the refracting power values of the first normal measurement.

20. A method according to claim 18, wherein the selected position corresponds to a refracting power value in a weak principal meridian of the eye to be examined calculated from the refracting power values of the first normal measurement.

21. A method according to claim 18, wherein the selected position corresponds to a refracting power value in a strong principal meridian of the eye to be examined calculated from the refracting power values of the first normal measurement.

22. A method according to claim 17, further comprising moving said target image, in said second fogging operation, in the direction in which accommodation of the eye to be examined is relaxed by a predetermined distance from said first position, and then performing said second normal measurement.

23. A method of measuring a refracting power of an eye to be examined, comprising the steps of:

performing a first preliminary measurement of a refracting power value in a predetermined meridian direction of the eye to be examined;

performing a first fogging operation for sequentially moving a target image in a direction in which accommodation of the eye to be examined is relaxed, based upon the refracting power value of the first preliminary measurement;

performing a first normal measurement of refracting power values in at least two meridian directions of the eye to be examined whose accommodation is relaxed by the first fogging operation;

determining astigmatic information of the eye to be examined, based upon the refracting power values obtained by the first normal measurement;

performing a second preliminary measurement of the refracting power value in the predetermined meridian direction of the eye to be examined, after moving said target image to a first position based upon the astigmatic information;

performing a second fogging operation for sequentially moving said target image in a direction in which accommodation of the eye to be examined is relaxed, based upon the astigmatic information of the eye to be examined and the refracting power value obtained in the second preliminary measurement; and performing a second normal measurement of the refracting power values in said at least two meridian directions of the eye to be examined whose accommodation is relaxed by said second fogging operation.

24. A method according to claim 23, further comprising the steps of:

obtaining a spherical power and a cylindrical power of the eye to be examined from the refracting power values of the first normal measurement;

setting an initial position of said target image at a set position which is moved from a selected position between a second position corresponding to the spherical power and a third position corresponding to the sum total of the spherical power and the cylindrical power, by a predetermined distance in a direction in which accommodation of the eye to be examined is relaxed; and performing the second fogging operation by sequentially moving said target image from the initial position in accordance with a change in the refracting power value of the second preliminary measurement with respect to the refracting power values of the first normal measurement in the predetermined meridian direction.

25. A method according to claim 24, wherein the selected position corresponds to an equivalent spherical value of the eye to be examined calculated from the refracting power values of the first normal measurement.

26. A method according to claim 24, wherein the selected position corresponds to a refracting power value in a weak principal meridian direction of the eye to be examined calculated from the refracting power values of the first normal measurement.

27. A method according to claim 24, wherein the selected position corresponds to a refracting power value in a strong principal meridian direction of the eye to be examined calculated from the refracting power values of the first normal measurement.

28. A method according to claim 23, further comprising moving said target image, in said second fogging operation, in the direction in which accommodation of the eye to be examined is relaxed by predetermined distance from said first positions, and then performing said second normal measurement.

29. A method according to claim 23, further comprising the steps of:

once moving said target image by a first predetermined distance in a direction opposite to the direction in which accommodation of the eye to be examined is relaxed; and then moving the image target by a second predetermined distance in the direction in which accommodation of the eye to be examined is relaxed, to perform a normal measurement.

30. An eye measuring apparatus comprising:

a refracting power detector to measure refracting power values of an eye to be examined in a plurality of meridian directions;

a target at which the eye to be examined gazes;

a calculator which calculates a position to which said target image is to be moved and at which accommodation of the eye to be examined is relaxed, in accordance with astigmatic information of the eye to be examined and the refracting power value measured in a predetermined one of the plurality of meridian directions, wherein the astigmatic information is based upon the refracting power values measured in at least two of the plurality of meridian directions and the refracting power value in the predetermined meridian direction takes into account the astigmatic information; and a driving device to move said target to said position calculated by said calculator.

31. An apparatus according to claim 30, wherein said refracting power detector, said calculator and said driving device constitute a feedback control mechanism, and wherein the feedback control mechanism:

performs a first preliminary measurement of the refracting power value in the predetermined meridian direction of the eye to be examined, performs a first fogging operation for sequentially moving said target in a direction in which accommodation of the eye to be examined is relaxed, based upon the refracting power value of the first preliminary measurement, performs a first normal measurement of the respective power values in said first meridian direction and said second meridian direction, which is different from the first meridian direction, of the eye to be examined whose accommodation is relaxed by said first fogging operation, performs a first calculation for calculating the astigmatic information of said eye to be examined based upon the refracting power values of said first normal measurement, moves said target to the first position on the basis of the astigmatic information calculated in said first calculation, performs a second preliminary measurement of the refracting power value in the predetermined meridian direction of the eye to be examined, while said target is in the first position, performs a second calculation for calculating a change in the refracting power value in said second preliminary measurement with respect to at least one of the refracting power values measured in said first normal measurement, performs a second fogging operation for sequentially moving said target in the direction in which accommodation of the eye to be examined is relaxed, based upon said change calculated in said second calculation, and performs a second normal measurement of the respective power values in said first meridian direction and said second meridian direction of the eye to be examined whose accommodation is relaxed by said second fogging operation.

32. An apparatus according to claim 30, further comprising a corneal shape detector to measure a corneal shape of the eye to be examined, while accommodation of the eye to be examined is relaxed.

33. An apparatus according to claim 32, wherein said refracting power detector, said calculator and said driving device constitute a feedback control mechanism, and wherein the feedback control mechanism performs:

a first preliminary measurement of the refracting power value in the predetermined meridian direction of the eye to be examined, a first fogging operation for sequentially moving said target in the direction in which accommodation of the eye to be examined is relaxed, based upon the refracting power value of the first preliminary measurement, a first normal measurement of the respective refractive power values in said first and second meridian directions of the eye to be examined whose accommodation is relaxed by said first fogging operation, a calculation of the astigmatic information of the eye to be examined based upon the refracting power values of said first normal measurement, a second preliminary measurement of the refracting power value in the predetermined meridian direction of the eye to be examined, after said target is moved to a first position based upon the astigmatic information, a second fogging operation for sequentially moving said target in the direction in which accommodation of the eye to be examined is relaxed, based upon the astigmatic information and the refracting power value measured in said second preliminary measurement, and a second normal measurement of the respective refracting power values in said first and second meridian directions of the eye to be examined whose accommodation is relaxed by said second fogging operation, wherein said corneal shape detector measures the corneal shape at least once, while accommodation of the eye to be examined is relaxed by one of said first and second fogging operations.

* * * * *

UNITED STATES PATENT AND TRADEMARK OFFICE
CERTIFICATE OF CORRECTION

PATENT NO. : 5,555,039
DATED : September 10, 1996
INVENTOR(S) : IKI et al.

It is certified that error appears in the above-indentified patent and that said Letters Patent is hereby corrected as shown below:

TITLE PAGE:

Section [75], change "Nobuyki" to --Nobuyuki--;

Section [56], change "5/1983" to --6/1983--;

Column 21, line 35, change "positions" to --position--.

Signed and Sealed this

Twenty-fourth Day of December, 1996

Attest:

BRUCE LEHMAN

*Attesting Officer*  *Commissioner of Patents and Trademarks*